United States Patent
Clouatre et al.

(10) Patent No.: US 10,561,630 B2
(45) Date of Patent: *Feb. 18, 2020

(54) HYDROXYCITRIC ACID COMPOUNDS AND CAPSULE LIQUID DELIVERY

(71) Applicant: GLYKON TECHNOLOGIES GROUP, LLC, Seattle, WA (US)

(72) Inventors: Dallas L. Clouatre, Seattle, WA (US); Daniel E. Clouatre, Seattle, WA (US)

(73) Assignee: GLYKON TECHNOLOGIES GROUP, LLC, Seattle, WA (US)

( * ) Notice: Subject to any disclaimer, the term of this patent is extended or adjusted under 35 U.S.C. 154(b) by 133 days.

This patent is subject to a terminal disclaimer.

(21) Appl. No.: 15/730,011

(22) Filed: Oct. 11, 2017

(65) Prior Publication Data

US 2018/0110750 A1   Apr. 26, 2018

Related U.S. Application Data

(60) Provisional application No. 62/412,393, filed on Oct. 25, 2016.

(51) Int. Cl.

| | | |
|---|---|---|
| *A61K 31/225* | (2006.01) | |
| *A61K 47/12* | (2006.01) | |
| *A61K 9/48* | (2006.01) | |
| *A61K 9/08* | (2006.01) | |
| *A61K 9/20* | (2006.01) | |
| *A61K 9/50* | (2006.01) | |
| *A61K 47/10* | (2017.01) | |
| *A61K 47/42* | (2017.01) | |

(52) U.S. Cl.
CPC .............. *A61K 31/225* (2013.01); *A61K 9/08* (2013.01); *A61K 9/2054* (2013.01); *A61K 9/48* (2013.01); *A61K 9/4808* (2013.01); *A61K 9/4816* (2013.01); *A61K 9/4825* (2013.01); *A61K 9/4858* (2013.01); *A61K 9/5057* (2013.01); *A61K 47/10* (2013.01); *A61K 47/12* (2013.01); *A61K 47/42* (2013.01)

(58) Field of Classification Search
CPC ............................ A61K 9/4825; A61K 9/5057
See application file for complete search history.

(56) References Cited

U.S. PATENT DOCUMENTS

| | | | |
|---|---|---|---|
| 2001/0036473 A1 | 11/2001 | Scott et al. | |
| 2006/0292216 A1 | 12/2006 | Clouatre et al. | |
| 2011/0301177 A1* | 12/2011 | Messerschmid | ..... A61K 9/4858 514/254.09 |
| 2016/0136117 A1 | 5/2016 | Clouatre et al. | |
| 2016/0279056 A1* | 9/2016 | Zhao | ................... A61K 9/0056 |

OTHER PUBLICATIONS

"Glycerol." Chemical Compounds. Retrieved Jun. 18, 2019 from Encyclopedia.com: https://www.encyclopedia.com/science/academic-and-educational-journals/glycerol.*

* cited by examiner

*Primary Examiner* — Kortney L. Klinkel
(74) *Attorney, Agent, or Firm* — Karl Bozicevic; Bozicevic, Field & Francis LLP

(57) ABSTRACT

A capsule oral delivery system is disclosed. The system includes an outer capsule completely enclosing an inner content, or a hard shell comprised of hydroxypropyl methylcellulose (HPMC) enclosing the content. A liquid formulation forming the inner content of the outer capsule is comprised of a hydroxycitric acid (HCA) salt, water, and glycerol, with the HCA being completely dissolved in the water and glycerol which may be the only components present in the capsule, which may be administered to a patient in a method of treatment to cause weight loss when repeatedly administered.

6 Claims, No Drawings

HYDROXYCITRIC ACID COMPOUNDS AND CAPSULE LIQUID DELIVERY

FIELD OF THE INVENTION

The invention relates to the use of food and pharmaceutical compositions containing (−)-hydroxycitric acid, its salts, amides and esters in delivery via soft gelatin capsules, liquid-filled hard shell capsules and related deliveries.

BACKGROUND OF THE INVENTION

Despite more than two decades of extensive sales in the dietary supplements market, (−)-hydroxycitric acid (HCA) (typically extracted from *Garcinia cambogia. G. atroviridis, G. indica* and related species) and its various salts continues to lack delivery methods leading to adequate dispersion of the HCA in the gut as described below using the extensive record of weight loss trials as examples. Beverage deliveries have not proven successful due to low amounts of active, lactone formation and binding to other ingredients. Tablet deliveries provide poor dispersion as shown by documented experience. A liquid-filled hard shell delivery was tried, but never made it into sustained commercialization and was abandoned in part due to costs and in part due to the requirement for excessively large ("000") capsules. Only two soft gelatin formats presently seem to be available commercially. Both simply coat HCA salts with fats (coconut and/or palm oil) and place a relatively small amount of the HCA salt, again, in a very large capsule. This approach duplicates many or all of the limitations of tablet and ordinary capsule deliveries.

Free (−)-hydroxycitric acid, calcium, magnesium and potassium salts of HCA and poorly characterized mixtures of two or more of these minerals, usually substantially contaminated with sodium—and, sometimes, even free chloride ion with only the sodium has been removed, currently exist on the American market. Calcium/sodium salts have been sold widely since at least as early as 1992. Most of the HCA sold to date consists of calcium salts of varying degrees of purity and, more recently, of poorly characterized calcium and potassium mixtures. For instance, the currently best selling HCA salt (potassium-calcium hydroxycitrate) typically contains ≥10 percent impurities and the product specification allows for approximately 25 percent±variations in the mg/gram of the potassium and calcium cations. (Shara M, Ohia S E, Schmidt R E, Yasmin T, et al. Physico-chemical properties of a novel (−)-hydroxycitric acid extract and its effect on body weight, selected organ weights, hepatic lipid peroxidation and DNA fragmentation, hematology and clinical chemistry, and histopathological changes over a period of 90 days. Mol Cell Biochem. 2004 May; 260(1-2):171-86.) Safety issues have been raised with regard to the free acid and lactone forms of HCA due to their strong chelating properties and the risk of excessive loss of zinc from the body, a concern especially important to males both in puberty and in the later stages of life.

HCA was very extensively studied by Hoffman-La Roche. Animal tests to establish the appetite suppressing effects of HCA found that a single large oral dose or two divided oral doses totaling approximately one-fourth the size of the single dose resulted in a 10% or greater reduction in food consumption in experimental animals fed a high-sugar diet. (Minimum doses were 2.63 mmoles/kg once per day or 0.33 mmoles/kg twice per day either one hour before meals or four hours after, but not after the last meal of the day.) This result continued over many weeks, but in no case beyond approximately seven weeks, with the chronic ingestion of HCA. The appetite control mechanism of HCA was said to not involve any conditioned aversion to food, i.e., HCA does not alter taste, cause gastric distress or illness, etc. Rather, this control was thought to stem from the increased production of glycogen and/or stimulation of glucoreceptors in the liver, either of which results in early satiety through signals sent to the brain via the vagus nerve. It has now been demonstrated experimentally that the Roche position that HCA suppresses appetite through vagal afferents associated with the liver almost certainly is mistaken. In an animal trial in which the hepatic branch of the vagus was severed (hepatic branch vagotomy), there was no significant effect found with this surgery in comparison with controls. (Leonhardt M, Hrupka B J, Langhans W. Subdiaphragmatic vagal deafferentation fails to block the anorectic effect of hydroxycitrate. Physiol Behav. 2004 Sep. 15; 82(2-3):263-8.)

Human research has provided, at best, only weak support for the Roche satiety findings, which were based on animal trials and mostly restricted diets, for instance, based predominantly on glucose. Early satiety with meals has been found only under very limited conditions. Ingesting tablets or capsules, even when there was significant weight loss, has not led to significantly advanced satiety. For instance, although 1,200 mg HCA daily given as tablets (2×400 mg 50% material as Citrin® calcium hydroxycitrate taken 3 times daily before meals) for 12 weeks led to significant weight loss, there was no significant change in food intake. The findings were 3.7±3.1 kg active versus 2.4±2.9 kg placebo. Over a 3-month period, these results of less than a pound of additional weight loss per month are hardly impressive; however, the difference is significant. (Mattes R D, Bormann L. Effects of (−)-hydroxycitric acid on appetitive variables. Physiol Behav. 2000 Oct. 1-15; 71(1-2):87-94.)

A more recent trial that utilized a diet normal in caloric intake, but reduced in fat and employing prepared meals, enforced exercise, and visual inspection of capsule consumption found significant weight loss, but mealtime satiety was increased over a period of many weeks rather than days. (Preuss H G, Bagchi D, Bagchi M, Rao C V, Dey D K, Satyanarayana S. Effects of a natural extract of (−)-hydroxycitric acid (HCA-SX) and a combination of HCA-SX plus niacin-bound chromium and Gymnema sylvestre extract on weight loss. Diabetes Obes Metab. 2004 May; 6(3):171-80.) At the end of eight weeks, appetite was decreased by approximately 15.6% in the group consuming 2,800 mg/HCA per day in capsules and by 21.2% in those consuming this amount of HCA plus other ingredients. Placebo experienced no reduction in appetite. Obviously, a certain percentage of the change in appetite in the active arms at the end of eight weeks can be attributed to weight loss rather than satiety per se. More telling, a trial described below using the same HCA source at only 900 mg/day, but delivered differently, reduced appetite by 15-30% in a mere two weeks.

The reductions in appetite and the other findings in the Preuss study also appear to be inflated by the failure to properly blind the trail. Put simply, the placebo used in the trial, microcrystalline cellulose, is a light filler having a bulk density of between 0.2 and 0.4 g/cc, whereas a calcium-potassium HCA salt has a bulk density of between 0.7 and 0.9 g/cc. Even in opaque capsules, it immediately would have been obvious to all involved which capsules contained placebo and which contained the actives. The failure of the blinding answers many of the questions that have been raised regarding this study (somewhat misleadingly published as several papers over a two-year period) conducted entirely in India under Indian conditions. For instance, despite boxed meals and enforced/supervised exercise in previously sedentary subjects, in the placebo arm there either was no benefit or even a trend upward for LDL, triglycerides and total cholesterol, whereas HDL trended downward. Bodyweight in placebo barely budged at either 4 or 8 weeks. In effect, there was no placebo response despite major interventions, any one of which normally produces significant results in LDL, HDL, triglycerides, total cholesterol, and body weight. To take but one parameter, the failure to show weight loss in placebo under these experimental conditions is out of line with the great preponderance of published studies. (Truby H, Baic S, deLooy A, Fox K R, et al. Randomised controlled trial of four commercial weight loss programmes in the UK: initial findings from the BBC "diet trials". BMJ. 2006 Jun. 3; 332(7553):1309-14.) Even taking the study at face value, the reductions in appetite reported were small and required many weeks to become important.

Human trials with HCA showing the rapid onset of meal-linked satiety are limited to only one study. Current HCA products have been shown to induce meal satiety (as opposed to reducing snacking) within a reasonable time period of days rather than weeks only under the very limited condition of being dissolved in 100 ml tomato juice just prior to ingestion timed approximately an hour before lunch and supper, then two hours after the evening meal to reduce snacking. In a trial published in 2002, although food intake decreased 15-30% there was no significant weight loss over a 2-week period. (Westerterp-Plantenga M S, Kovacs E M. The effect of (−)-hydroxycitrate on energy intake and satiety in overweight humans. Int J Obes Relat Metab Disord. 2002 June; 26(6):870-2.) The researchers themselves noted the problematic nature of HCA delivery by way of the observation "Prevention of degradation and bio-availability was documented." The satiety found in this study using much smaller amounts of HCA than in Preuss 2004 (900 mg vs. 2800 mg) not only appeared far more quickly, but was more powerful than that reported in the 2004 Indian study even at the end of the 8 week trial.

The foregoing studies are representative. The only reasonable conclusion that can be drawn from the literature available on HCA in humans is that there is little impact on meal satiety when the compound is delivered via capsules or tablets if the relevant period is counted in days rather than weeks. To date, satiety has been demonstrated in humans only when HCA is dissolved and delivered in a substantial amount of tomato juice approximately an hour before meals. Capsules and tablets have proved to be ineffective for inducing meal satiety. Indeed, despite the Indian trial described above and published as several papers in 2004 and 2005, two of the leading American researchers in the field of bariatrics in 2007 continued to express skepticism regarding the viability of HCA as a diet product. (Bray G A, Greenway F L. Pharmacological treatment of the overweight patient. Pharmacol Rev. 2007 June; 59(2):151-84.)

Delivering meal satiety with HCA under the only approach shown to work, i.e., mixing in a large volume of tomato juice just before consuming 60 minutes prior to meals, is extremely onerous. The components of this approach include a) preventing degradation of the HCA, b) insuring the complete release of the HCA, and c) insuring bioavailability of the HCA. Degradation is a major issue. Not one of the proposed ready-to-drink HCA preparations or HCA "waters" that have been marketed has succeeded, in large part because of degradation. HCA, as is well established, very readily binds to gums, fibers and pectins. It also binds to many phytochemicals, such catechins and polyphenols more generally. Leaving HCA in prepared beverage preparations, especially those that have been heat pasteurized, encourages these reactions and also induces the rapid formation of the HCA lactone. The lactone is almost totally ineffective for satiety and other health purposes. (Lowenstein J M, Brunengraber H. Hydroxycitrate. Methods Enzymol. 1981; 72:486-97.) However, the lactone does have at least one negative impact—it has a type of toxicity, probably due to its binding zinc and leading to its excretion from the body. The lactone is labile to the acid, so the chelation most likely is due to the free acid. (Burdock G, Soni M, Bagchi M, Bagchi D. *Garcinia cambogia* toxicity is misleading. Food Chem Toxicol. 2005 November; 43(11):1683-4; author reply 1685-6. Erratum in: Food Chem Toxicol. 2007 March; 45(3):515.) Studies by other researchers utilizing fully reacted HCA salts have found no toxicities.

The other two issues of complete release and bioavailability, similarly, pose daunting challenges. Westerterp-Plantenga and Kovacs chose tomato juice as a vehicle precisely because its pH would insure that the HCA salt was fully dissolved. By using a relatively high volume vehicle, they also insured that the dissolved salt would be exposed to any possible receptors in the stomach and intestine as well as allowing for better uptake. In this sense, their approach replicates the usually successful delivery of HCA by gavage. It is not accidental that no one has been able to duplicate Westerterp-Plantenga and Kovacs' results by means of other forms of delivery until now.

As demonstrated by the foregoing, the issues of degradation, complete release and bioavailability are not successfully addressed by current HCA deliveries. It clearly is desirable to find better solutions. The Inventors propose a solution that can be implemented via soft gelatin capsules, liquid-filled hard shell capsules and a number of other dosage forms.

SUMMARY OF THE INVENTION

A desirable delivery for HCA includes stability/non-lactone formation, avoidance of agents that bind HCA and introduce food effect issues, and some form of pre-solubilization allowing rapid and complete distribution into the gastro-intestinal system. Capsules, tablets and current soft gelatin capsule forms all fail to deliver one or more of these qualities and often lead to unwanted vehicle footprints in the form very large capsules or a challenging number of smaller capsules for the required dosage. The Invention provides a novel and, indeed, surprising approach that pre-solubilizes the HCA salt payload without danger of lactonization, binding or dependence on large amounts of carrier(s), hence can be very compact. HCA salts are insoluble or virtually insoluble in glycerin, which makes the formulation of the present invention an unexpected discovery over the prior art. The formulation of the invention comprises, and preferably consists only of an HCA salt, glycerin and water inside a soft gelatin capsule. Inasmuch as glycerin in combination with HCA at this level is of less than optimal compatibility with animal gelatin, the capsule may further consist of hydroxypropyl methylcellulose (HPMC) or a related biocompatible cellular derivative with water solubility. Liquid-filled hard shells and certain other oral delivery forms are enabled by this Invention.

The invention comprises a gelatin or hard shell capsule in the form of an oral delivery system for delivering a salt of hydroxycitric acid (HCA). The oral capsule completely encloses the inner content which is a liquid formulation comprising, consisting essentially of, or consisting only of a salt of HCA, water and glycerol in ratio amounts such that the HCA salt is completely dissolved in the water and glycerol with the optional inclusion of a monoterpene such as limonene. The liquid formulation is prepared by mixing glycerol in water wherein the glycerol is present in an amount of about 1-3 parts by volume and the water is present in an amount of about 3-1 parts by volume to create a solution, and dissolving the HCA salt in the solution wherein the HCA salt is present in the concentration ranging from 1.1 to 1.7 molar dosage, wherein the salt may be a potassium-magnesium salt.

The Invention further includes a method of treatment which comprises administering to a subject a capsule which may be a gelatin capsule or a hard shell capsule providing an oral delivery system with the outer capsule completely enclosing the inner contents and the inner contents comprising, consisting of, or consisting only of an HCA salt, water, and glycerol formulated as described herein to obtain a high concentration of the HCA salt in the liquid formulation which has been encapsulated.

In this Invention, HCA delivered in the form of its potassium or potassium-magnesium salt is efficacious at singly delivered dosages of between 1 and 5 grams, preferably at a dosage of between 2 and 3 grams for most individuals. Other salts, amides and esters are active at individual dosage ranges, with, for instance, the sodium salt acting similarly to the potassium salt whereas salts containing calcium are less active. The dosage preferably should be given twice daily 30-60 minutes prior to meals with other regimens for special purposes and circumstances.

An aspect of the invention includes a method for delivering hydroxycitric acid from one or more stable hydroxycitrate salts suitable for delivery by means of soft gelatin capsules and liquid-filled hard shell capsules.

Another aspect of the invention is the above method wherein the hydroxycitrate salt is selected from a group consisting of sodium, potassium, potassium-magnesium and magnesium hydroxycitrate; double and triple-metal salts based on counter ions magnesium, potassium and sodium; and biocompatible combinations thereof.

Another aspect of the invention is the above method in which the hyrdoxycitric acid dissolved in a water-glycerol mixture consisting of 25% glycerol to form a dense core.

Another aspect of the invention is the above method in which the selected sources of hydroxycitric acid (HCA) salt are used to form the filling for the core of a confectionary product.

DESCRIPTION OF THE PREFERRED EMBODIMENTS

Before the present HCA oral delivery formulations are described, it is to be understood that this invention is not limited to particular formulation described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a capsule" includes a plurality of such capsules and reference to "the HPMC" includes reference to one or more biocompatible equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Various salts of (−)-hydroxycitric acid (calcium, magnesium, potassium, sodium and mixtures of these) have been available commercially for several years. A base formula that can be scaled with appropriate adjustments and used in deliveries such as soft gelatin capsules, liquid-filled hard gelatin capsules and other formats involves only three ingredients: pure potassium-magnesium HCA (best at approximately 69.7% HCA), glycerol and purified water. Another transition metal, such as zinc, can replace magnesium and be prepared in the same manner. Likewise, sodium is roughly interchangeable for potassium. Calcium-containing salts, such as potassium-calcium HCA, can be prepared, but require additional steps and larger volumes due to the poorer solubility of calcium compared with magnesium. Impure salts containing residual gums, fibers, pectins and protein present significant challenges and may not be suitable for preparation. The capsule composition represents another issue. Animal gelatin capsules exhibit a poor tolerance for glycerin-based formulations and are challenged by the hygroscopic characteristics of soluble HCA salts that have been pre-solubilized. Capsule should consist of hydroxypropyl methylcellulose (HPMC) or similar materials, such as seaweed derived alternatives.

These and other objects, advantages, and features of the invention will become apparent to those persons skilled in the art upon reading the details of the gelatin capsule system as more fully described below.

The present disclosure provides a formulation for use in hard or soft capsules, such that capsules filled with the formulation can be prepared and stored without significant degradation, erosion, swelling or dissolution of the capsule shell during the acceptable shelf-life of the filled capsule. For example, the capsules of the invention can be filled with the liquid solution of a highly concentrated salt of hydroxycitric acid and undergo 5% or less degradation over a period of 6 months or more, or 12 months or more and exhibit 5% or less capsule degradation. Any shell forming material suitable for use in hard or soft shell capsules or the encapsulation of a fill formulation can be used in the present invention. In some instances, a capsule includes a liquid drug-containing fill composition enclosed within a capsule shell. The term "shell" as used herein is taken to mean the shell of a capsule dosage form or the encasement or encapsulation material used to encapsulate formulations and fill compositions.

The fill composition or liquid formulation may be encased by two types of capsules: hard shell capsules and soft shell capsules. Hard shell capsules and soft shell capsules differ in their thickness, amount of cross-linking, rigidity, composition, shape and other ways. Accordingly, a formulation suitable for filling a soft shell capsule might not be suitable for filling a hard shell capsule and vice versa. In some instances, a capsule may contain another small capsule or a tablet along with granules. The granules may be made up of beads or other forms, which may contain more than one type of drug molecules, and specifically the various aqueous formulations of hydroxycitric acid salts as described herein. This way, more than one type of drug may be combined in the same capsule. In some instances, all the drugs reside in the capsule core and there is no drug in the capsule shell composition.

There are two basic embodiments to the invention with one being a gelatin capsule and the other being a hard shell capsule. The liquid formulation of HCA can be used to fill a hard shell capsule. Gelatin soft capsules can be formed around the liquid HCA formulation.

In some instances, the capsule shell for use in the subject systems and methods is a hard capsule shell. The hard capsule shell retains its shape and it is dry in nature. In some instances, there is nothing inside core portion of the capsule shell as the capsule shell may be filled with a liquid fill composition. The capsule shell may be prepared using a film-forming composition/matrix. The hard capsule shell includes two parts—a body in the core of which holds the contents of the dosage form, such as, powders/granules/beads/pellets/a mini-tablet/a mini-capsule/liquid formulations and a cap, which fits on the body of the capsule shell and acts as a cover (U.S. Pat. Nos. 4,510,168 and 4,532,881). Apart from the main constituent of the capsule shell being gelatin or polymeric in nature, the shell also contains other excipients such as plasticizers (e.g., polyethylene glycol, sorbitol, glycerol), stabilizers (antimicrobial and antioxidants), colorants (FD&C colors, titanium dioxide, natural dyes including riboflavin, carotenes, turmeric and caramel) and sequestering agents (citric acid, sodium citrate, and ethylenediaminetetraacetic acid). The hard capsule shells may be purchased from capsule suppliers.

There are various sizes of hard capsule shells available ranging from sizes '000' to '5' (higher the number, smaller is the dose volume), the most commonly used are sizes '0' and '1'. The fill weight of granules having a density of 0.7 g/mL is 475 mg and 350 mg for size '0' and '1' capsules, respectively. Size '000' capsules can contain 960 mg of core material loaded with medicament. The average weights of size '1' and '0' empty hard gelatin capsule shell are 76 mg and 96 mg, respectively.

A range of different capsule sizes can be used for both the gelatin and hard capsules used in connection with the invention. The capsules can contain any desired amount of the liquid formulation of HCA, and may for example be designed such that the capsule holds 100 mg to 1000 mg of HCA, or 200 mg to 800 mg HCA, or approximately 500 mg HCA, ±20%, ±10% or ±5%.

In treating a patient, the patient may be dosed with one or more capsules at each dosing event. The dosing may be once a day, twice a day, three times a day or more. The total per day dosing may range over any desired range based on the needs of the patient and can be, for example, from 100 mg per day to 5000 mg per day of HCA.

In one embodiment, the dosage is in a range of from 3000 mg to 4500 mg per day. The dosage is delivered with capsules which comprise 750 mg of HCA salt per capsule. Those capsules may be administered in the amount of 4 to 8 capsules per day or 6 capsules per day providing a dosage of about 4.5 grams per day of HCA salt to the patient in order to effectively induce weight loss.

One skilled in the art of formulation will determine the stability of the drug in the capsule shell composition during manufacture and storage.

In certain embodiments, the polymers that can be used in making empty, hard capsule shells can be divided into the following groups: 1) Cellulose- or cellulose compounds, which include, but are not limited to, cellulose, cellulose ether, methyl cellulose, hydroxypropyl methyl cellulose, hydroxypropyl cellulose, hydroxyethyl vcellulose, carboxymethyl cellulose, cellulose acetate phthalate, 2) starch-based compounds, which include, but not limited to hydroxyethyl starch, hydroxypropyl starch, hydroxyethyl methyl starch, 3) carrageenans-kappa and iota, 4) Acrylate compounds, which include, but not limited to, polyacrylate, polymethylacrylate, poly(acrylate-methylacrylate), poly (methylacrylate-methyl methacrylate), 5) polyolefins, which include, but limited to, polyvinyl chloride, polyvinyl alcohol, and polyvinyl acetate and 6) pullulan (a polysaccharide polymer consisting of maltotriose units). The empty, hard capsule shell can also be a laminate where the drug-loaded layer is either inner or outer. The non-drug loaded layer can have a function such as, an enteric coated layer or a layer to control drug diffusion as a result of swelling. In some instances, materials suitable for the preparation of the capsule shell include but are not limited to gelatin, starch, animal gelatin, agar, fish (piscine) gelatin or a combination thereof. Essentially any material known to those of ordinary skill in the art as being for the preparation of capsule shell can be used in a capsule according to the invention.

In some instances, empty hard shell capsules may be produced by the following methods: pin dip-coating or heat-melting. A liquid mass is produced by dissolving the capsule compositions in a solvent system or by melting at an appropriate temperature. In the pin dip-method, a plurality of pins maintained at a certain temperature dip in the solution and is withdrawn at a pre-determined rate while spinning. The pins coated with capsule composition are then dried at a gradual rate at a suitable temperature. The body and cap of the capsules are separated from the pins and then trimmed to an exact length. The method has been employed to prepare the body and cap of the capsules. The body and cap are joined together and a logo is printed, if necessary. U.S. Pat. No. 2,526,683 discloses a process for preparing methyl cellulose medicinal capsules by a dip coating process. In the heat-melting method, the hard shell or capsule may be formed by heating a capsule forming composition (preferably in powdery form) in a mold, followed by inserting a pestle into the mold to coat the melted capsule forming composition onto the pestle. The hard capsule shell thus formed, after hardened and dried, is removed from the pestle.

A hard capsule dosage form may be manufactured by filling the core of the hard capsule shell with powders, granules, beads, pellets, a tablet, another capsule, or a liquid fill composition. The fill composition, which may be a water-containing composition, can be a gel, syrup, fluid, semi-solid, solid, suspension, emulsion, paste, or glassy material. In some instances, the capsule dosage form includes a hard hydroxypropyl methylcellulose capsule shell and a liquid formulation including a potassium-magnesium salt of hydroxycitric acid (HCA), water, and glycerol, whereby the HCA salt is completely dissolved in the water and glycerol. The hard shell capsule dosage form may be filled with a liquid formulation and sealed by any suitable manual, semi-automatic, or automatic filling machine and equipment known in the art. Suitable machines for use in filling hard capsules may include dosator machines and dosing-disc machines. The filling of the hard shell capsule may be performed by a capsule filling machine for liquid filling of the type available, for example, from Holfiger and Kars, Zanasi Nigris, Parke-Davis and Co., Eli Lilly and Co., Robert Bosch Corp., among others. The hard shell capsules are generally sealed by one of several methods. The filled capsule may be sprayed with a water alcohol mixture to seal the cap to the body of the container. Alternatively, the cap may be sealed to the body of the container by a bonding process, which entails passing the cap over a revolving wheel immersed in a water gelatin or a cellulose bath and then passing the capsule through a drying chamber to seal the gap between the cap and the body of the capsule with dried gelatin or cellulose. The bonding is generally performed on commercially available machines.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Dissolving HCA

In order to produce the most effective capsules of the invention, it is preferable to obtain a relatively high concentration of HCA salt inside the capsules. In one embodiment, this is best obtained by first mixing the glycerol in water. The amount of water and glycerol mixed together are important to obtaining preferred results. The glycerol is present in an amount of about 1 to 3 parts by volume relative to about 1 to 3 parts by volume of water in order to create a desired solution. It may be desirable to include larger amounts of water such as 1.5, 2, or 3 parts of water by volume, relative to 1 part of glycerol. After the solution is obtained, the HCA salt is dissolved in the solution of water and glycerol to obtain high concentration of the HCA salt. The concentration can range from about 1.1 to 1.7 molar and the salt may be any pharmaceutically acceptable salt but is preferably potassium-magnesium salt of HCA.

With respect to each of the examples below, the amounts can vary ±20%, ±10%, ±5%, or ±1%.

Example 1

| | Base Formula | |
|---|---|---|
| Item # | Ingredient per Capsule | Amount (mg/capsule) |
| 1 | Potassium-Magnesium HCA Salt | 750 |
| 2 | Glycerol (25% in Purified Water) | ~1 mL |

Batch size will be determined by equipment and the number of capsules desire.

A. Blend glycerol with purified water until dissolved completely.

B. Dissolve the potassium-magnesium hydroxycitrate into the glycerol/water component.

C. The resulting should be quite thick; viscosity can be varied as required by altering the amount of glycerol/water used. Soft gelatin capsules can be formed in the normal fashion and liquid-filled hard shells filled.

(Optional) in this example as well as others, due to viscosity issues, it may be necessary for filling a hydroxypropyl methylcellulose hard capsule to add a small amount of a monoterpene, such as limonene, to the fill material inside of the capsule. Those skilled in the art will adjust the amount of the monoterpene as needed based on nozzle size and filling speed desired. Although the amount can vary, it may be less than 10% by volume of the total volume of the filling, 5% or less, or 1% or less.

Example 2

| | Base Formula | |
|---|---|---|
| Item # | Ingredient per Capsule | Amount (mg/capsule) |
| 1 | Sodium HCA Salt | 600 |
| 2 | Glycerol (25% in Purified Water) | ~1 mL |

Batch size will be determined by equipment and the number of capsules desire.

A. Blend glycerol with purified water until dissolved completely.

B. Dissolve the sodium hydroxycitrate into the glycerol/water component.

C. The resulting should be quite thick; viscosity can be varied as required by altering the amount of glycerol/water used. Soft gelatin capsules can be formed in the normal fashion and liquid-filled hard shells filled.

Example 3

| Base Formula | | |
|---|---|---|
| Item # | Ingredient per Capsule | Amount (mg/capsule) |
| 1 | Potassium HCA Salt | 700 |
| 2 | Glycerol (25% in Purified Water | ~1 mL |

Batch size will be determined by equipment and the number of capsules desire.

A. Blend glycerol with purified water until dissolved completely.

B. Dissolve the potassium hydroxycitrate into the glycerol/water component.

C. The resulting should be quite thick; viscosity can be varied as required by altering the amount of glycerol/water used. Soft gelatin capsules can be formed in the normal fashion and liquid-filled hard shells filled.

Example 4

| Base Formula | | |
|---|---|---|
| Item # | Ingredient per Capsule | Amount (mg/capsule) |
| 1 | Magnesium HCA Salt | 800 |
| 2 | Glycerol (25% in Purified Water | ~1 mL |

Batch size will be determined by equipment and the number of capsules desire.

A. Blend glycerol with purified water until dissolved completely.

B. Dissolve the magnesium hydroxycitrate into the glycerol/water component.

C. The resulting should be quite thick; viscosity can be varied as required by altering the amount of glycerol/water used. Soft gelatin capsules can be formed in the normal fashion and liquid-filled hard shells filled.

Example 5

A Confectionery Formulation

The HCA combination of any of Examples 1-4 readily can be incorporated into various confections based on centers or cores. Experimentally, the combination is easily contained in centers including sugars and alcohol sugars such as sucrose, maltose, trehalose, isomaltose, sorbitol, xylitol and so forth. (Gums, pectins and similar binders, however, are to be avoided.) The core must be surrounded by a barrier against moisture, but that barrier should not consist of items that dissolve easily in water-glycerol mixtures. The solution is initially to apply coatings of sugar or polyols to the core by means known to those skilled in the art. Subsequently, a second coating of a fat-based or waxy edible, such as chocolate (or variations such as chocolate and tea extracts), is applied to complete the process with a moisture barrier. The range of centers possible is limited only by the skill and art of the flavor master. HCA has been shown to dramatically slow the crossing of glucose from the gut into the blood, hence there is little fear of inducing blood sugar spikes with these combinations.

CONCLUSION (−)-Hydroxycitrate presents special challenges to delivery by means of soft gelatin capsules and liquid-filled hard shell capsules. A desirable delivery for HCA includes stability/non-lactone formation, avoidance of agents that bind the compound and introduce food effect issues, and some form of pre-solubilization allowing rapid and complete distribution into the gastro-intestinal system. The Invention overcomes these challenges by means of a water-glycerol carrier leading to the creation of a dense and compact product suitable for encapsulation.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A gelatin capsule oral delivery system, comprising:
an outer capsule comprised of gelatin completely enclosing an inner content;
a liquid formulation forming the inner content of the outer capsule, the formulation consisting essentially of a salt of hydroxycitric acid (HCA), water, and glycerol, whereby the HCA salt is completely dissolved in the water and glycerol;
wherein the liquid formulation is prepared by mixing glycerol in water wherein the glycerol is present in an amount of about 1 to 3 parts by volume and the water is present in an amount of about 3 to 1 parts by volume to create a solution;
dissolving hydroxycitrate salt in the solution wherein the hydroxycitrate salt is present in a concentration ranging from about 1.1 to 1.7 molar dosage.

2. The gelatin capsule oral delivery system of claim 1 wherein the hydroxycitrate salt is a stable hydroxycitrate salt selected from a group consisting of sodium, potassium, potassium-magnesium or magnesium hydroxycitrate; double- or triple-metal salts based on the counter ions selected from the group consisting of magnesium, potassium and sodium; and any workable combination thereof.

3. The gelatin capsule oral delivery system of claim 2, wherein the hydroxycitrate salt is a potassium-magnesium salt of ( )-hydroxycitric acid and is present in an amount of 750 mg.

4. A hydroxypropyl methylcellulose capsule oral delivery system, comprising:
- an outer capsule comprised of hydroxypropyl methylcellulose completely enclosing an inner content;
- a liquid formulation forming the inner content of the outer capsule, the formulation consisting essentially of a potassium-magnesium salt of hydroxycitric acid (HCA), water, and glycerol, whereby the HCA salt is completely dissolved in the water and glycerol;
- wherein the liquid formulation is prepared by mixing glycerol in water wherein the glycerol is present in an amount of about 1 to 3 parts by volume and the water is present in an amount of about 3 to 1 parts by volume to create a solution;
- dissolving hydroxycitrate salt in the solution wherein the hydroxycitrate salt is present in a concentration ranging from about 1.1 to 1.7 molar dosage.

5. The hydroxypropyl methylcellulose capsule oral delivery system of claim 4 wherein the hydroxycitrate salt is a stable hydroxycitrate salt selected from a group consisting of sodium, potassium, potassium-magnesium or magnesium hydroxycitrate; double- or triple-metal salts based on the counter ions selected from the group consisting of magnesium, potassium and sodium; and any workable combination thereof.

6. The hydroxypropyl methylcellulose capsule oral delivery system of claim 4, wherein the hydroxycitrate salt is a potassium-magnesium salt of ( )-hydroxycitric acid.

* * * * *